United States Patent [19]
Nikitin et al.

[11] Patent Number: 5,757,477
[45] Date of Patent: May 26, 1998

[54] REAL TIME MONITORING OF MEDIUM PARAMETERS

[75] Inventors: Petr Nikitin; Anatolii Beloglazov, both of Moscow, Russian Federation

[73] Assignee: Ceram Optec Industries Inc., East Lungmeadow, Mass.

[21] Appl. No.: 423,021

[22] Filed: Apr. 17, 1995

[51] Int. Cl.⁶ .................................................. G01N 21/41
[52] U.S. Cl. ...................... 356/128; 356/432; 356/445; 257/431
[58] Field of Search .................. 356/445, 432, 356/128; 257/431, 449

[56] References Cited

U.S. PATENT DOCUMENTS 4,482,779  11/1984  Anderson ......................... 257/431
4,555,622  11/1985  Glass et al. ....................... 257/431
4,556,790  12/1985  Glass et al. ....................... 257/431

OTHER PUBLICATIONS

B. Liedberg, C. Nylander, I. Lundström, "Surface Plasmum Resorance for Gas Detection and Biosenting", 4 Sensura & Actuators, 299–304, (1983), (no month).

Primary Examiner—Richard A. Rosenberger
Attorney, Agent, or Firm—Bolesh J. Skutnik

[57] ABSTRACT

The invention relates to non-contact methods of examining physical and chemical parameters of various media, particularly, gases or liquids. It can be used to determine properties and compositions of media including those containing various chemical or biological components with applications in scientific research, technology and environmental monitoring.

24 Claims, 6 Drawing Sheets

REAL TIME MONITORING OF MEDIUM PARAMETERS

BACKGROUND OF THE INVENTION

1. Field of the Invention

The invention relates to non-contact methods of studying physical and chemical parameters of various media, particularly, gases or liquids. It can be used to determine properties and compositions of media including those containing various chemical or biological components with applications in scientific research, technology and environmental monitoring.

2. Information Disclosure Statement

The known method to measure parameters of media containing chemical or biological components, which is most closely analogous to the proposed one, comprises specification of reference relationships between a response signal and the medium state parameters, action by electromagnetic radiation up on one of the sides of a structure made of a metal film deposited on a substrate, said medium being placed from the side of the metal film with respect to said structure, excitation of a surface electromagnetic wave (SEW) in the metal film, and generation of a response signal from said structure, one judging the measured parameters from comparison of said signal with the reference relationships [B. Liedberg, C. Nylander and I. Lundstrom "Surface plasmon resonance for gas detection and biosensing", Sensors and Actuators, 4 (1983) 299–304]. The value of the measured medium parameter is obtained from recording the position of the resonance maximum of a SEW excitation efficiency or relative value of the SEW excitation efficiency within the slope of the resonance.

The associated apparatus for measuring parameters of media containing chemical or biological components, which is most closely analogous to the proposed one, comprises an electromagnetic radiation source, a solid structure including a metal film serving for exciting a SEW in it, deposited on a substrate, and an information processing unit [B. Liedberg, C. Nylander and I. Lundstrom].

The advantage of the mentioned method and the apparatus is a non-destructive and non-disturbing action of measurement tools upon a medium tested. This enables one to solve a wide range of problems for various media testing. However, the response signal is here a purely optical signal resulting from changing parameters of a radiation beam reflected from the metal film under conditions of resonant SEW excitation in the film To record a response signal associated with the reflected radiation beam, there is a need for a registration channel including an optical arrangement with a photodetector unit. A corresponding measuring setup has to include either a mechanical angular scanning system with a reflected light spot displacement compensation or a photodetector matrix registering the divergent reflected beam passed through a special optics. This makes an overall device rather cumbersome, complicated and expensive, and, in a number of cases, restricts the device's capabilities (particularly, accuracy and resolution limit) and the area of possible applications. These are significant intrinsic drawbacks of the mentioned method and the associated apparatus.

OBJECTS AND SUMMARY OF THE INVENTION

It is an object of the proposed invention to provide improved method and apparatus for measurement of parameters of a medium.

Another object of the invention is to provide an improvement in accuracy and resolution limit of measurements and also to extend the range of measured parameters and the area of possible applications.

Still other object of the invention is to provide convenient, fast and inexpensive monitoring through utilizing of compact and inexpensive measuring tools which could be batch-fabricated on the base of conventional microelectronics technologies.

The above, and other objects, features and advantages of the present invitation will become apparent from the following description read in conjunction with the accompanying drawings.

DESCRIPTION OF PREFERRED EMBODIMENTS

Figure 1:
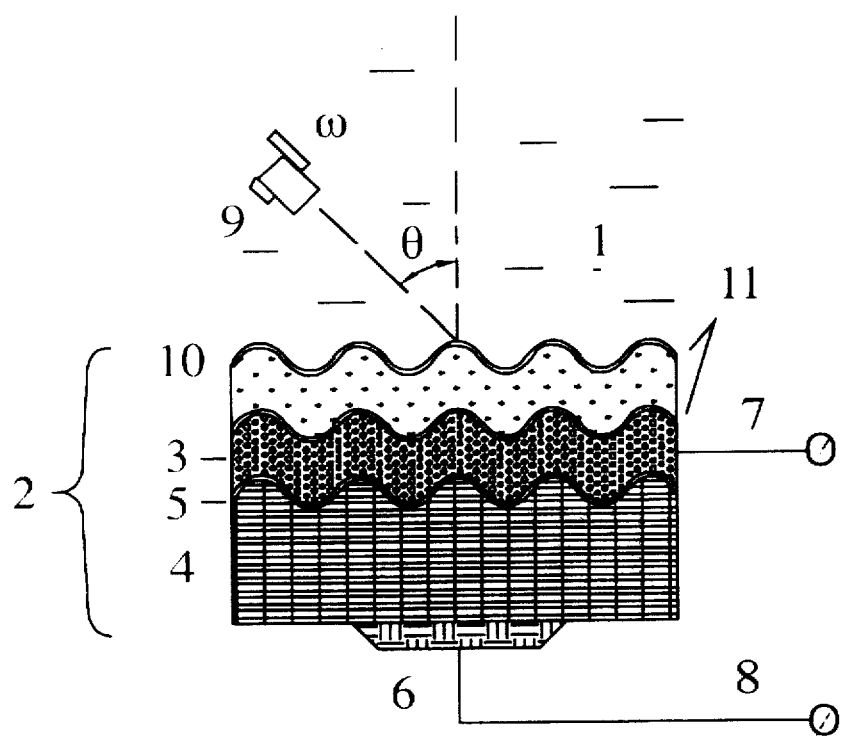
FIG. 1 shows a schematic to realize the proposed method.

In order to achieve the goals of this invention in the proposed method, a semiconductor is used as the substrate on which the metal film is deposited immediately or via an interface layer to form a structure. An electric signal which is used as a response signal from the structure is supplied to a circuit connected to the metal film and the semiconductor. The electric signal is recorded within the slope of the resonant dependence of the signal value on, at least, one of the direction coordinates and/or the frequency of the electromagnetic radiation. The radiation beam may be collimated, or divergent, or convergent, as well as monochromatic or non-monochromatic. It may also be linearly polarized and may be delivered directly or through an optical fiber. To extend the dynamic range of measurements, one varies an angular coordinate of the direction of the radiation beam relative to the structure or the radiation frequency.

To increase the accuracy and the selectivity of the measurements, a layer of a substance with the predetermined dependencies of its parameters on values and types of an external action (e.g., tested medium action) may be placed on or over the surface of the metal film opposite to the semiconductor. In particular, at least, one layer of a substance may be placed on or over the surface of the metal film for binding, at least, one component of the medium To excite SEW in the metal film by means of the most compact and the simplest tools, the surface of the metal film, opposite to the semiconductor, may be spatially modulated.

To achieve an object of the invention in the associated apparatus, the used substrate is made of a semiconductor, and the inputs of the information processing unit are connected to the metal film and the substrate. The metal film and the semiconductor substrate are combined in a solid structure with or without an intermediate layer between them where, for example, the latter has a resistivity greater than that of the metal In both cases, the interface(s) may be spatially modulated fully or partially.

The electromagnetic radiation source may be capable of changing a radiation frequency and/or direction of propagation relative to said solid structure.

To excite a SEW, the metal film surface opposite to the semiconductor is spatially modulated, or the apparatus is equipped with a component (e.g., a prism) which ensures total internal reflection of the radiation from its output side. There may be a gap between the output side of the component and the surface of the metal film, in which a layer of a substance, whose refraction index is less than that of a medium of said component, can be placed.

A layer of a substance with the predetermined dependencies of its parameters on values and types of an external action (e.g., tested medium action) may be placed on or over the surface of the metal film opposite to the semiconductor. The apparatus may be provided with, at least, one layer of a substance for binding, at least, one component of the medium, the layer being placed on or over the surface of the metal film.

The apparatus may be placed in a tested medium or be equipped with a medium container which part transmitting the radiation beam, in a number of cases, is made in a form of a wedge.

In addition, the apparatus may be provided with a radiation polarizer and/or an optical fiber to supply the radiation.

It is worth to emphasize that, in the proposed method and the apparatus, a SEW is excited in the metal film on the semiconductor substrate and the electric signal coming immediately from the metal and the semiconductor is recorded. Hence the one solid structure comprises, in this case, both the sensitive element of a measuring device and a photodetector, avoiding the need to measure the parameters of a reflected radiation beam. Consequently, there is no additional channel for recording any optical signal in contrast to the method of the prototype causing the drawbacks mentioned above. The whole proposed apparatus (excluding an information processing unit) is simply an optoelectronic pair—a hybrid circuit which parts could be made by microelectronics industry. Thus, the proposed method and apparatus have apparent advantages over the known ones for providing more simple and cheap technique of measurement in a wide range of parameters, extending the area of possible applications and improving the accuracy and resolution of measurements through utilizing tools which are compact, cheap and batch-fabricated on the base of conventional microelectronics technologies.

Figure 2:
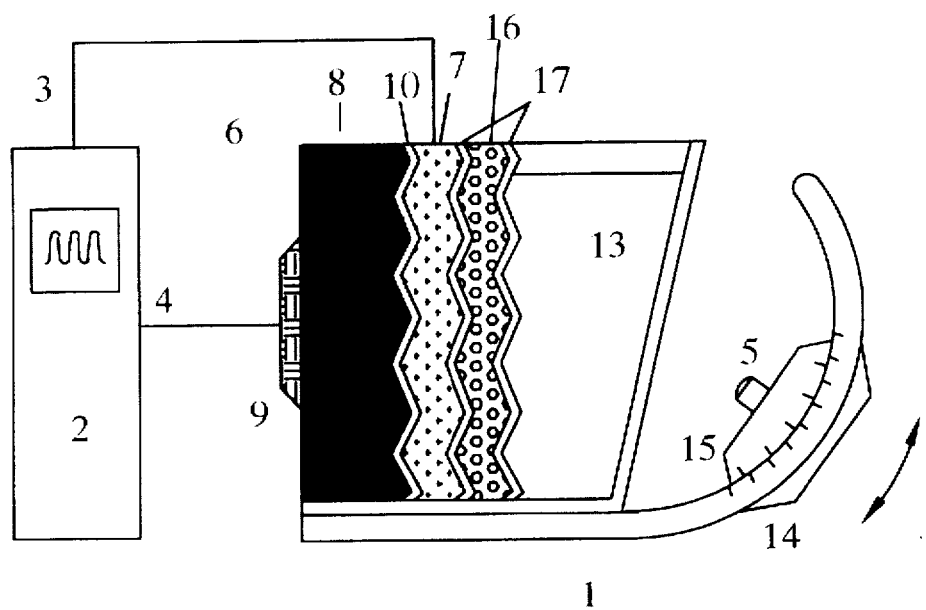
FIG. 2 illustrates a preferred embodiment using the exciting of a SEW by means of a spatial modulation (grating) on a metal surface whose tested medium is placed in a special cuvette which uses a surface of a sensitive solid structure as one of the walls.
Figure 3:
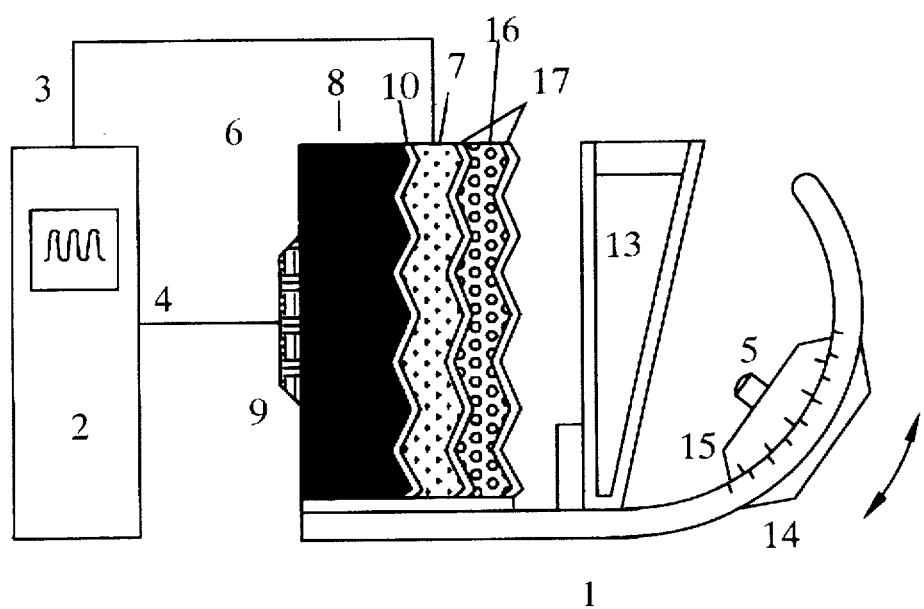
FIG. 3 illustrates another preferred embodiment using the exciting of a SEW by means of a spatial modulation (grating) on the metal surface in the case when the tested medium is placed in a wedge cuvette which may be removable or not, situated at a definite distance from the surface of a sensitive solid structure.
Figure 4:
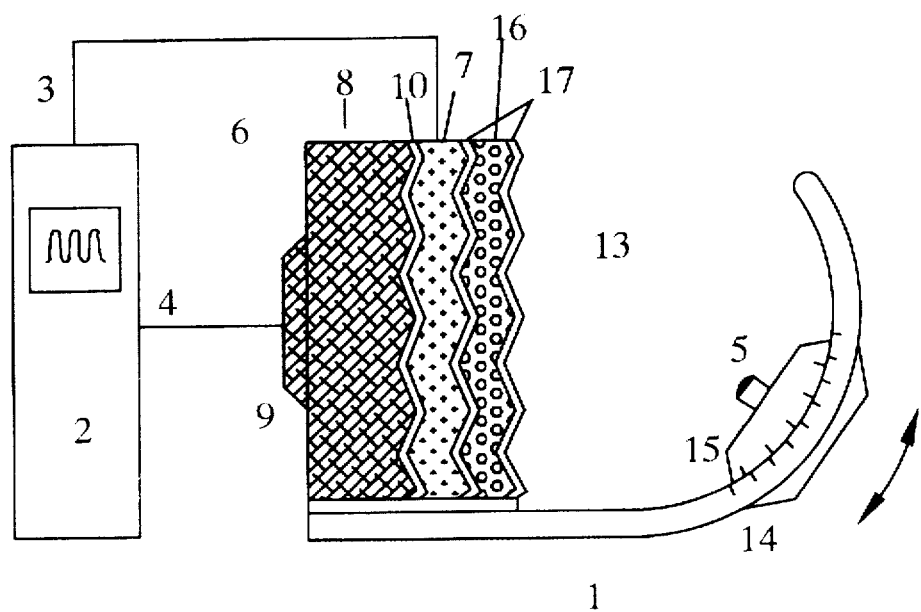
FIG. 4 illustrates a preferred embodiment using the exciting of a SEW by means of a spatial modulation (grating) on a metal surface where there is no cuvette, a measuring head being put in the tested medium.
Figure 5:
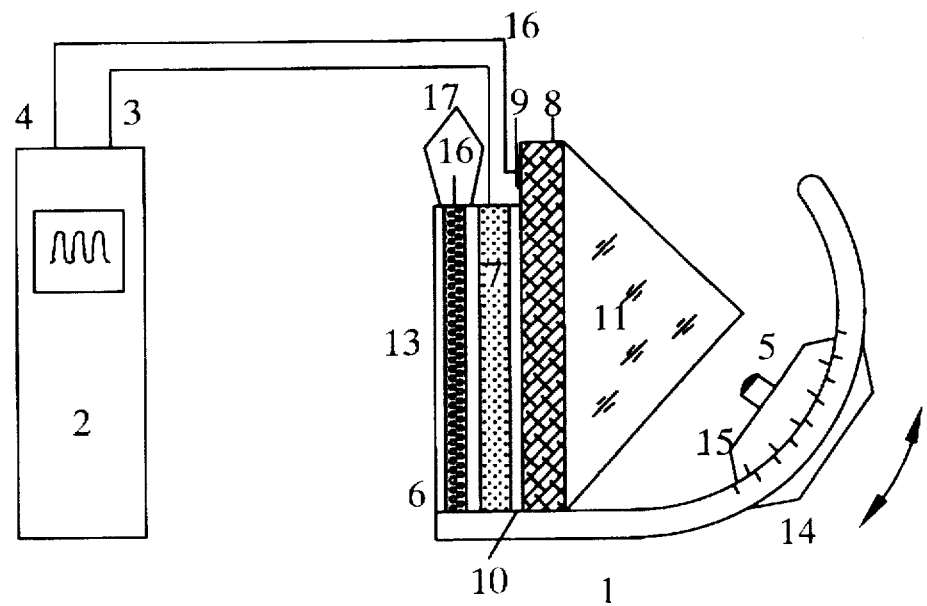
FIG. 5 illustrates other embodiments based on attenuated total internal reflection technique whose radiation is supplied from a side of a semiconductor layer deposited onto the output side of a prism, the measuring head being equipped with a cuvette or not.
Figure 6:
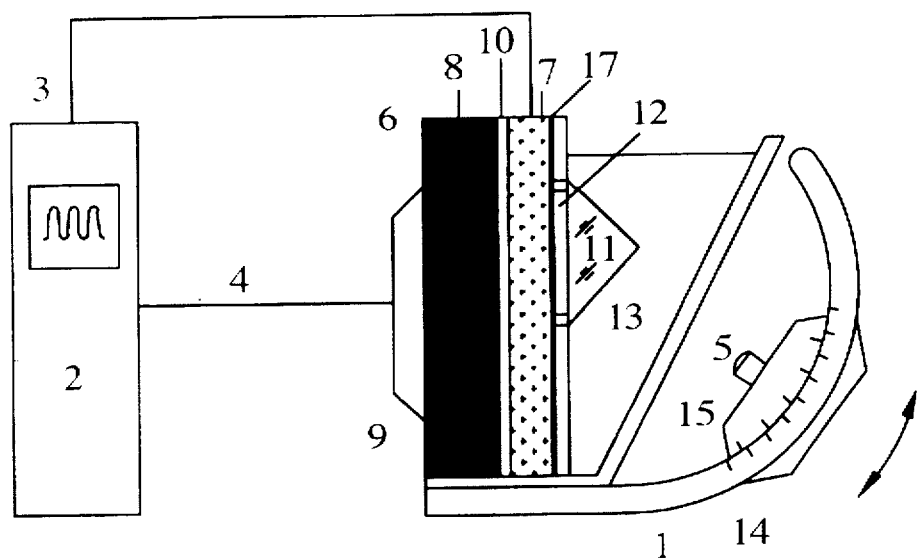
FIG. 6 illustrates still other preferred embodiments based on attenuated total internal reflection technique where there is an arrangement with a wedge cuvette
Figure 7:
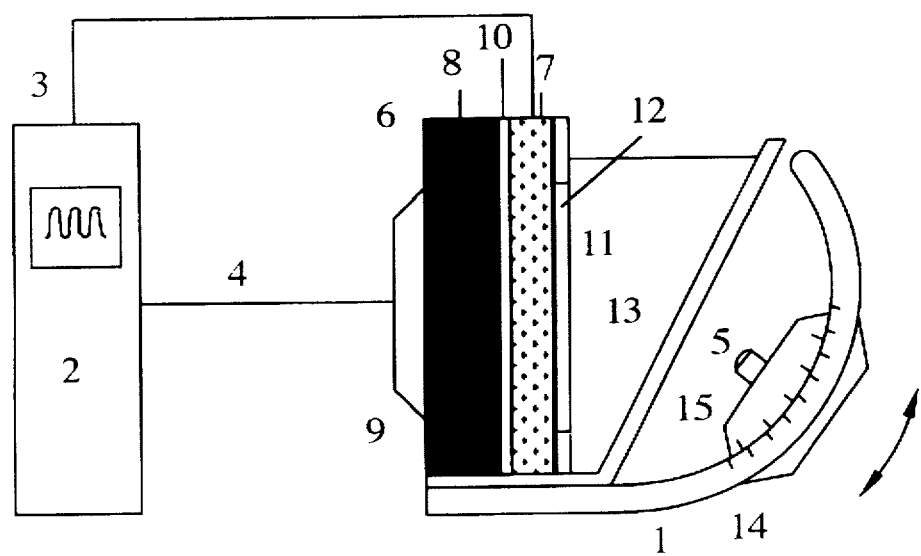
FIG. 7 illustrates additional preferred embodiments based on attenuated total internal reflection technique where there is a total internal reflection from the output side of the tested medium.
Figure 8:
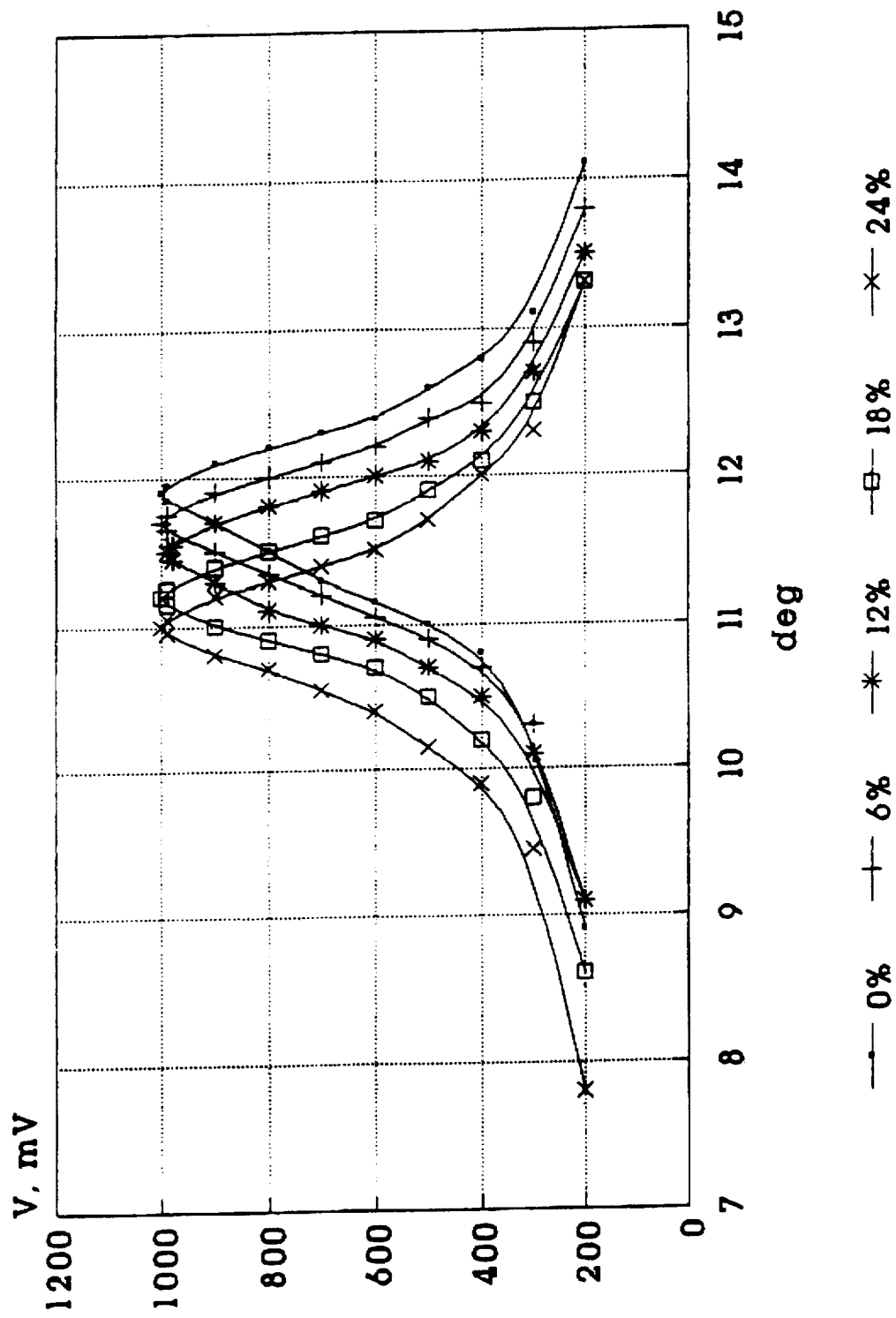
FIG. 8 shows a dependence of a response signal on the angular coordinate of the direction of radiation incidence onto a metal film
Figure 9:
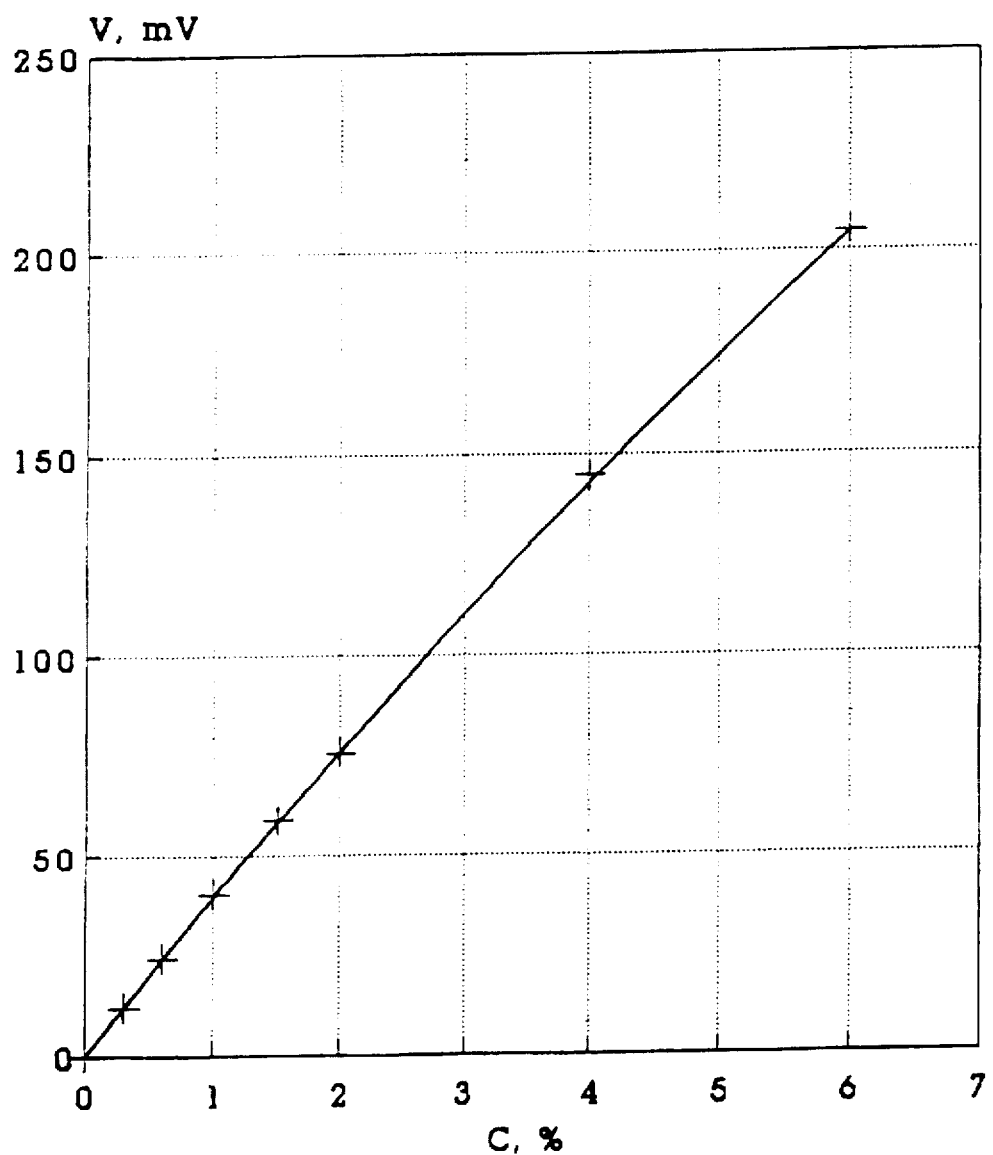
FIG. 9 shows a dependence of the response signal on a particular parameter of a medium to be tested.

A schematic to realize the proposed method is shown in FIG. 1. FIGS. 2-7 illustrate the variants of the proposed apparatus. Particularly, in FIGS. 2-4 there are variants using the exciting of a SEW by means of a spatial modulation (grating) on the metal surface. In FIGS. 5-7 there are those based on the principle of attenuated total internal reflection. In FIG. 2, the tested medium is placed in a special cuvette which uses the surface of the sensitive solid structure as one of the walls. In FIG. 3, it is placed in a wedge cuvette which may be removable or not, situated at a definite distance from the surface of the sensitive solid structure. In FIG. 4, there is no cuvette, a measuring head being put in the tested medium. In FIG. 5, radiation is supplied from a side of a semiconductor layer deposited onto the output side of a prism, the measuring head being equipped with a cuvette or not. In FIG. 6, there is an arrangement with a wedge cuvette. In FIG. 7, there is a total internal reflection from the output side of the tested medium, the variant of FIG. 7 using a cuvette for the tested medium. Dependences of the response signal on the angular coordinate of the direction of radiation incidence onto the metal film are depicted in FIG. 8. In FIG. 9, there is a dependence of the response signal on a particular parameter of a medium tested.

The proposed method is realized as follows (FIG. 1). Medium 1 to be tested is allowed to contact solid structure 2. The most important parts of the latter are metal film 3 and semiconductor substrate 4. Between them, there may be thin intermediate layer 5. Sometimes, the latter may be introduced to obtain a desired value of the resistance of the metal—semiconductor junction. Film 3 and substrate 4 with ohmic contact 6 are provided with electric outputs 7 and 8, respectively, which serve to connect structure 2 to a measuring circuit as a photoelement or a photodiode. A related electric signal is recorded.

Medium 1 may be placed in a cuvette, or structure 2 may be put in medium 1. Important is only that, at least, a part of medium 1 is situated on a side of film 3, opposite to semiconductor 4.

Electromagnetic radiation coming from source 9 (as a rule, visible or infrared) excites a SEW at a surface of film 3, nearer to medium 1. The excitation of the SEW is accompanied with the resonant enhancement of the electric signal. Recording this signal and analyzing its peculiarities (e.g. value within the slope of the resonance or the angular or spectral position of the resonance) in relation to reference relationships dependent on a medium parameter, one determines the value of the latter.

The method is based on the following physical mechanism. It is known, that a SEW at a media interface, particularly, of a metal (e.g. film 3) and a dielectric (e.g. medium 1) can be excited via coupling an incident p-polarized electromagnetic radiation coming from source 9 by means of a prism $$kn_{prism} \sin \theta = k_{SEW} \quad (1),$$

or a grating on the metal (film 3) surface:

$$kn \sin \theta + mG = k_{SEW} \quad (2)$$

The designations are:

$k=\omega/c=2\pi/\lambda$ is an incident light wave vector of a wavelength $\lambda$ in vacuum.

n—a refraction index of the tested medium 1, $kn_{prism}$—a refraction index of the prism, θ—angle of radiation incidence onto the grating or the output side of the prism (0<θ<90°), m—positive or negative integer, G=2π/Λ—a reciprocal lattice vector of the grating with a period Λ.

$$k_{SEW} = \pm (2\pi/\lambda)[\epsilon'_{Me} n^2/(\epsilon'_{Me}+n^2)]^{1/2} \quad (3),$$

where "+" relates to m>0, "−" does to m<0, is a SEW wave vector. Here $\epsilon'_{Me}=\text{Re}(\epsilon_{Me})$ is a real part of a metal permittivity at the light frequency ω ($\epsilon'_{Me}<0, |\epsilon'_{Me}|>n^2$).

Relations (1) and (2) describe the position of the resonant maximum of the coupling efficiency (part of the energy of radiation transformed into that of SEW), dependent on k, n and θ. When one of these parameters is allowed to change (e.g., n) the resonance position changes (resonant k and θ). When a parameter is changed within the slope of the resonant curve the coupling efficiency changes dramatically. In this connection, there follows a method of determining n of the medium adjacent to film 3.

For one thing, n of the medium can be determined through measuring values of θ and ω corresponding to the resonance of the efficiency of radiation coupling to SEW at medium 1—metal 3 interface. Then, from calculated or experimental reference relationships between resonance values of θ and ω and refraction index n, one can find the value of the latter.

For another thing, one can fix θ and ω corresponding to the slope or the resonance curve of the coupling efficiency for the medium with a known n=$n_0$. The value of n for tested medium 1 is to be found with respect to $n_0$ through measuring the difference of related to n and $n_0$ values of the coupling efficiency within the slope of the resonance curve and comparing it with the proper reference relationship.

From a practical standpoint, it is more convenient to measure not the coupling efficiency itself but some signal dependent on it.

Such a signal is very easy to obtain when the metal film 3 is combined with substrate 4 made of a semiconductor. In this case, the radiation to SEW coupling efficiency governs the value of the electric signal taken from outputs 7 and 8 which are connected immediately to film 3 and substrate 4. Film 3 and substrate 4 form structure 2 which is analogous to a traditional Schottky photodetector. As the latter, structure 2 can be connected up as a photoelement or a photodiode. A distinctive property of structure 2 is that the signal taken from it has a resonant maximum under the conditions of SEW excitation at medium—metal interface.

There may be a different character of the relation between the SEW and the electric signal, depending on the specific operating mechanism A mechanism discussed in [S. R. J. Brueck, V. Diadiuk, T. Jones and W. Lenth. "Enhanced quantum efficiency internal photoemission detectors by grating coupling to surface plasma waves". Applied Physics Letters, 46 (1985) 915–917] was based on absorption of the SEW in the metal film, generation of hot charge carriers in it and emission of them into the semiconductor through the Schottky barrier. Such carriers were affected by the barrier electric field in the semiconductor and resulted in the electric response signal taken from the structure. The energy of the radiation quantum was less than the energy gap of the semiconductor. It was mentioned that, under this condition, the radiation to excite the SEW could be supplied to the metal film both through the air and through the semiconductor.

When the energy of the radiation quantum is greater than the energy gap of the semiconductor, electron—hole pairs in the semiconductor can be produced, resulting from the penetration of the SEW into the semiconductor and/or from reconversion of the SEW to a radiation at the metal- semiconductor interface and absorption of this radiation in the semiconductor. Electron-hole pairs are separated by the Schottky barrier field and result in a photoresponse. It is obvious that, in this case, the radiation to excite the SEW can be supplied only from the side opposite to the semiconductor.

Thus, one can determine the refraction index n of medium 1 through measuring the position of the resonance maximum of a photosignal taken from the structure combining metal 3 and semiconductor 4 under SEW excitation conditions and comparing this position with the reference one in the dependence on the radiation direction angular coordinate relative to structure 2 or on the radiation frequency. Within the slope of the resonance curve, another regime is preferable. When radiation direction or frequency is fixed within the slope of the correspondent resonant dependence of the photosignal, the structure operates as an immediate converter of n to the photosignal. Consequently, measuring the photosignal and comparing it with the predetermined dependence of it on n enables one to find the value of n. In this regime, the sensitivity to n is proportional to the steepness of the slope. The dynamic range of measured n is, in contrast, proportional to the width of the resonant curve. The width is contributed by a radiation divergence and a spectral bandwidth of radiation source 9. To achieve a maximum sensitivity one should use monochromatic and collimated radiation. To extend the dynamic range, a divergent (convergent) or spectrum-broadened radiation can be used.

It is obvious that the above discussed concept for measuring n of medium 1 adjacent to film 3 can be extended to any medium parameter related to n. In particular, this holds for a medium density and concentration of an impurity component. To apply the proposed method, tested medium 1 and film 3 are not obligatory to be in contact. On the surface of metal film 3, there may be a layer 10 (FIG. 1) with specified relationships between its parameters and type and/or value of an external action, particularly, the action from medium 1. The most relevant example is layer 10 binding in a selective manner particles of component of medium 1 whose concentration is to be measured. It may be a specific phthalocyanine for nitrogen oxides sensing in a gas, an antigen to bind antibodies for immunosensing, and so on. Layer 10 can be used along with other layers 11 on its surface and/or on metal 3. Auxiliary layers 11 may serve to protect metal 3 or layer 10 from aggressive medium components, to improve adhesion or for other ancillary purpose. The SEW wave vector in such a multilayer system cannot be described by the simple expression (3). The dependence of $k_{SEW}$ on n still takes place, weakening as the total thickness of layers 10 and 11 between metal 3 and medium 1 increases. For a very great total thickness, the resonance position depends on n only through the tangential component knsinθ of the radiation wave vector incident upon the grating in relation (2) or through the appropriate radiation wave vector component incident upon a prism When the radiation to excite a SEW is supplied from the side of the semiconductor, the total thickness of layers 10 and 11 exceeding greatly the SEW penetration depth into them, the resonance position depends on measured medium parameters through the refraction index of an adequately chosen layer 10 rather than through n. In all the cases, the proposed method still applies.

In principle, the method could be realized on the base of a SEW excited at a surface of metal film 3 nearer to semiconductor 4, providing adequate values of permittivities are known. However, such a SEW has much less sensitivity to parameters of medium 1 because of strong decaying of the SEW intensity in depth of metal 3.

The proposed method is applicable not only to refraction index-dependent parameters of medium 1 but polarization-related ones as well. In particular, this is true for the concentration of a polarization-active component of medium 1. If the polarization rotation value for radiation passing medium 1 depends on a medium parameter to be measured, the polarization component that contributes to a SEW and, consequently, a signal value will depend on this parameter too. Here one has to use a linearly polarized radiation.

For a number of purposes, it is worth to supply a radiation to medium 1 through an optical fiber. It ensures a simple radiation direction adjustment and may be good to test explosive media. The following apparatus is put forward to demonstrate how to realize the proposed method (FIGS. 2–7).

Apparatus to measure medium parameters comprises the following elements: measuring head 1, information processing and indication unit 2 and connection wires 3 and 4.

The measuring head is made as an optoelectronic pair consisting of a radiation source and a detector.

As electromagnetic radiation source 5 (as a rule, visible or infrared), a built-in semiconductor light emitting device or the output end of an optical fiber is preferably to be used. This ensures the measuring head to be compact.

As a radiation detector, solid structure 6 is used. Its principal elements are metal film 7 (e.g., Ag, Au, Al, Cu) and semiconductor substrate 8 (e.g., Si, GaAs, InP). Wire 3 is connected to metal film 7, wire 4 connects to substrate 8 through ohmic contact 9. Structure 6 may include intermediate layer 10 (e.g. $SiO_2$) which is introduced, sometimes, between film 7 and substrate 8, in particular, to obtain a desirable resistance of the metal - semiconductor junction and is not critical for the apparatus operation. The interface of metal 7 and semiconductor 8, or, at least, one of the surfaces of layer 10 may be spatially modulated (e.g., periodically rippled) to enhance scattering a SEW from metal 7 into semiconductor 8. To excite a SEW on a surface of metal film 7 opposite to the semiconductor with the grating technique, this surface is spatially modulated, e.g., in the form of a sine-like grating (FIGS. 2–4). To excite a SEW with the technique of attenuated total internal reflection, prism 11 is used in the scheme of FIG. 6, which is rigidly bound with structure 6 forming gap 12 between them, according to the standard Otto technique for SEW excitation. Gap 12 is filled with a dielectric medium (particularly, with tested medium 13 itself) whose refraction index is less than that of prism 11. Arrangement in FIG. 7 is also based on the Otto technique where a wedge layer of tested medium 13 passed by a radiation beam serves as a prism, having a refraction index greater than that of the substance in gap 12. In FIG. 5, a gap between prism 11 and film 7 is filled with a semiconductor layer which serves as substrate 8. Such an arrangement corresponds to the Kretschmann technique for SEW excitation. If the radiation from source 5 is slightly absorbed in the material of substrate 8, substrate 8 and prism 11 may be a single unit of a semiconductor (not shown).

Radiation source 5 may be frequency tunable and/or angle adjustable to scan the direction of radiation incidence with respect to structure 6. In FIGS. 2–7, the ability of angular scanning and taking readings is schematically shown by angular scale 14 with auxiliary scale 15. By frequency tuning and angular scanning of the radiation source, one can adjust the apparatus and obtain reference relationships. Instead of angular scales, an angular position potentiometer detector is preferable. It converts directly readings of angular position to an electric signal. Near the output of source 5, there may be a polarizer and/or a set of lenses (not shown).

In all the variants, it is essential that tested medium 13 is placed from the side of the metal film with respect to structure 6. In all the variants except that in FIG. 5, the radiation beam coming from source 5 to film 7, passes through medium 13.

In the schemes of FIGS. 2, 4, 5, medium 13 may be in a contact with film 7 or be separated from it by intermediate layers 16, 17. As a material of layer 16, one can use a substance which possesses a desirable response when affected by tested medium 13, in particular, binds (adsorbs or absorbs) the examined component of medium 13. Layer 17 may be an auxiliary one, e.g., to protect film 7 or layer 16, to improve adhesion or other ancillary purposes.

In the schemes of FIGS. 6–7, medium 13 may not contact film 7 except in FIG. 6 when medium 13 with a refraction index less than that of prism 11 also fills gap 12. In these cases as well as in the schemes of FIG. 7 gap 12 may contain also layers 16, 17 of adequate thicknesses and refraction indices.

In the schemes of FIGS. 3, 6, when medium 13 is separated from film 7 with a distance much greater than a SEW penetration depth and the substance passed by the radiation before and after cuvette 18 is the same, it is necessary that a layer of medium 13 passed by the radiation has the form of a wedge. This form ensures a dependence of the conditions of a SEW excitation in film 7 on the refractive properties of medium 13.

A variant shown in FIG. 5 is worthwhile to examine, namely a slightly transparent and scattering media analogously to [B. Liedberg, C. Nylander and I. Lundstrom] without transmitting radiation through them, by means of a SEW only.

The apparatus operates as follows. The resonant maximum of the efficiency of a SEW excitation at the surface of metal film 7 opposite to substrate 8 is accompanied with the resonant maximum of the electric signal supplied through wires 3 and 4 to information processing unit 2, as discussed in details above in the description of the proposed method. By examining the dependencies of this signal on $\omega$, $\theta$, or polarization of radiation at different values of a tested medium parameters and relating them to the predetermined reference relationships, one can find the value of the parameter of interest. When the apparatus is adjusted to be within the resonance of the electric signal at all variations of the measured parameter dealt with, the apparatus operates as an immediate converter of the measured parameter value to the electric signal. Provided proper calibration, the measured values can be indicated by unit 2.

The proposed method and apparatus have been applied to measure the concentration of sucrose in distilled water. A sucrose water solution to be tested was placed in a 23° wedge cuvette in the arrangement of FIG. 3 not using layers 16 and 17. The cuvette was attached to a grated Ag/n-GaAs Schottky barrier photodetector. It had a grating period of 0.46 μm. The p-polarized laser beam of a wavelength 0.63 μm passing through the cuvette had a power 1.65 mW and a divergence 0.65°. The light beam angular position respective to the normal to the Ag surface was measured with an accuracy of 0.05°. A reverse bias of 1.4 V was applied to the photodetector connected to a measuring scheme as a photodiode with a 40 k$\Omega$ load resistance.

Reference relationships of different kind have been obtained. Dependencies of a voltage signal on an incidence angle coordinate α (counted from the normal to the Ag surface) are depicted in FIG. 8 for several known sucrose concentrations. Comparing the maximum position for unknown concentration with those for known ones in FIG. 8, one can find the concentration value of the unknown. On detecting the maximum position at α=11.15°±0.05°, we found the corresponding concentration to be 19.5%±1.5%. A dynamic range in this regime of measurements is, in principle, unlimited. The accuracy is restricted by a technique of angular scanning and reading.

To determine concentration values more accurately, we have taken other reference relationships at fixed values of the angle α. The dependence of a voltage signal shift relative to the level of 800 mV (taken with the opposite sign) on sucrose concentration is shown in FIG. 9 for the fixed angle α=12.2° corresponding to the level of 800 mV for a pure water in FIG. 8. Within the accuracy of 0.5 mV, the dependence is linear between 0% and 1.5% with a factor of 40 mV/percent. After detecting angular position of the maximum signal for an unknown concentration to be 11.85°±0.05° which is near that for pure water, we then changed water in the cuvette under the conditions of FIG. 9 for the tested concentration solution. Measuring a signal of 43±0.5 mV, we found from FIG. 9 the tested concentration to be 1.075%±0.013%.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for measuring parameters of a medium which comprises the steps of:
   a. specifying a reference relationship between a response signal and medium parameters;
   b. fabricating a composite structure which comprises a metal film deposited on a semiconducting substrate and said medium positioned on a side of said metal film facing away from said semiconducting substrate;
   c. creating an electrical circuit in said composite structure between said metal film and said semiconducting substrate;
   d. illuminating said composite structure with electromagnetic radiation;
   e. exciting a surface electromagnetic wave in said metal film;
   f. placing on said composite structure at least one additional object or means which influences said surface electromagnetic wave and whose influence is dependent on said medium's parameters;
   g. creating a response signal in said composite structure as an electric signal which arises in a circuit between said semiconducting substrate and said metal film;
   h. measuring said response signal;
   i. comparing said response signal with said reference relationships to determine parameters of said external action acting on said sensitive material.

2. The method according to claim 1, having an additional step, within said fabrication step, of
   introducing at least a partial spatial modulation into at least one surface of said metal film thereby enhancing said creation of a response signal.

3. The method according to claim 1, having an additional step, within said fabrication step, of:
   introducing an intermediate layer whose resistivity is greater than that of said metal film between said metal film and said semiconducting substrate.

4. The method according to claim 1, having an additional step, within said placement step, of:
   placing a layer of a substance on a surface of said metal film facing away from said semiconductor substrate, wherein said substance layer has specified relationships between said substance layer's parameters, type or value and an external action applied at said layer.

5. The method according to claim 1, having an additional step, within said placement step, of:
   placing a layer of a substance on a surface of said metal film facing away from said semiconductor substrate, wherein said substance layer has binding sites for at least one component of said medium.

6. The method according to claim 1, having an additional step, within said illumination step, wherein said electromagnetic radiation has a propagation direction relative to said composite structure, of:
   varying an angular coordinate of said electromagnetic radiation's propagation direction relative to said composite structure.

7. The method according to claim 1, having an additional step, within said illumination step wherein said electromagnetic radiation has a frequency or a range of frequencies, of:
   varying said electromagnetic radiation's frequency.

8. The method according to claim 1, having an additional step, within said illumination step, of:
   providing said electromagnetic radiation as an energy beam, selected from the following: a divergent beam, a convergent beam, or a collimated beam.

9. The method according to claim 1, having an additional step, within said illumination step, of:
   providing said electromagnetic radiation as an energy beam, selected from the following: a monochromatic beam, a non-monochromatic beam, or a linearly polarized beam.

10. The method according to claim 1, where said illumination step is carried out by transmitting said electromagnetic radiation through an optical fiber onto said composite structure surface in contact with said medium.

11. The method according to claim 1, having an additional step of:
    monitoring a derivative electrical signal which corresponds to a slope of a resonance curve defining a dependence of said response signal on at least one of said radiation's propagation direction coordinates or of said radiation's frequency.

12. A photodetection device for measuring parameters of a medium which comprises:
    a source of electromagnetic radiation;
    a composite structure comprising a metal film deposited on a semiconducting substrate such that in operating said device a surface electromagnetic wave is created in said metal film;
    at least one additional object or means which influences said surface electromagnetic wave and whose influence is dependent on said medium's parameters;
    said at least one additional object or means being in contact with said metal film on a surface facing away from said semiconducting substrate;
    an information processing unit; and
    inputs of said information processing unit are connected one to said metal film and another to said semiconducting substrate.

13. A device according to claim 12, wherein at least one surface of said metal film has been at least partially, spatially modulated.

14. A device according to claim 12, which further comprises:

an intermediate layer between said metal film and said semiconducting substrate, said intermediate layer having a resistivity greater than that of said metal film.

15. A device according to claim 14, wherein at least one surface of said intermediate layer is at least partially, spatially modulated.

16. A device according to claim 12, wherein at least one surface of said intermediate layer is at least partially, spatially modulated.

17. A device according to claim 12, which further comprises:

a means to vary and select a frequency of said source of electromagnetic radiation.

18. A device according to claim 12, which further comprises:

said electromagnetic radiation has a propagation direction relative to said composite structure; and a means to change said propagation direction of said electromagnetic radiation relative to said composite structure.

19. A device according to claim 12, which further comprises:

a layer between said metal film and said medium, creating an interface between said metal film and said medium; and said layer having a refractive index such that said electromagnetic radiation is totally internally reflected at said interface.

20. A device according to claim 12, which further comprises:

a means to polarize a beam of electromagnetic radiation propagating from said electromagnetic radiation source.

21. A device according to claim 12, wherein an optical fiber is said electromagnetic radiation source, transmitting electromagnetic radiation from a remote source.

22. A device according to claim 12, wherein said object is a layer of a substance on a surface of said metal film facing away from said semiconductor substrate, wherein said substance layer has specified relationships between said substance layer's parameters, type or value and an external action applied at said layer.

23. A device according to claim 12, wherein said object is a layer of a substance on a surface of said metal film facing away from said semiconductor substrate, wherein said substance layer has binding sites for at least one component of said medium.

24. A device according to claim 12, wherein said means is a volume of said medium to be tested, said volume, being illuminated with electromagnetic radiation, having a wedge shape.

* * * * *